(12) United States Patent
Triva (10) Patent No.: US 10,550,362 B2
(45) Date of Patent: Feb. 4, 2020

(54) DEVICE AND METHOD FOR AUTOMATIC PROCESSING OF CULTURE PLATES FOR MICROBIOLOGICAL SAMPLES

(71) Applicant: COPAN ITALIA S.P.A., Brescia (IT)

(72) Inventor: Daniele Triva, Bovezzo (IT)

(73) Assignee: Copan Italia S.p.A., Brescia (IT)

( * ) Notice: Subject to any disclaimer, the term of this patent is extended or adjusted under 35 U.S.C. 154(b) by 932 days.

(21) Appl. No.: 14/787,202

(22) PCT Filed: Apr. 23, 2014

(86) PCT No.: PCT/IB2014/060933
§ 371 (c)(1),
(2) Date: Oct. 26, 2015

(87) PCT Pub. No.: WO2014/174455
PCT Pub. Date: Oct. 30, 2014

(65) Prior Publication Data
US 2016/0083686 A1    Mar. 24, 2016

(30) Foreign Application Priority Data

Apr. 26, 2013    (IT) .............................. MI2013A0692

(51) Int. Cl.
*C12M 1/36*    (2006.01)
*C12M 1/22*    (2006.01)
(Continued)

(52) U.S. Cl.
CPC ............ *C12M 41/48* (2013.01); *C12M 23/10* (2013.01); *C12M 33/00* (2013.01); *C12M 41/06* (2013.01); *C12M 41/46* (2013.01); *C12N 1/20* (2013.01)

(58) Field of Classification Search
CPC ...... C12M 41/48; C12M 23/10; C12M 23/50; C12M 23/52; C12M 33/00; C12M 41/06;
(Continued)

(56) References Cited

U.S. PATENT DOCUMENTS 5,961,923 A    10/1999    Nova et al.
6,002,789 A    12/1999    Olsztyn et al.
(Continued)

FOREIGN PATENT DOCUMENTS

DE    102010060634    5/2012
FR    2789694 A1    8/2000
(Continued)

OTHER PUBLICATIONS

PCT International Search Report and Written Opinion of the International Searching Authority, PCT/IB2014/060933, dated Jul. 3, 2014, 11 pages.
(Continued)

*Primary Examiner* — William H. Beisner
*Assistant Examiner* — Danielle B Henkel
(74) *Attorney, Agent, or Firm* — Fish & Richardson P.C.

(57) ABSTRACT

An automatic processing device of culture plates (2) including a support frame (3); a slide (4) for removably housing a culture plate (2) and movably mounted on the support frame (3) selectively displaceable between a first loading position, a plurality of image-acquiring positions, and a first unloading position; a camera (6) of a linear type, provided with telecentric optic (7) and a trilinear sensor, and arranged acquire a multiplicity of linear images of corresponding linear portions of an upper surface of the culture plate (2), during the displacing of the slide (4); a first lighting device (11) orientated such as to illuminate the linear portions of an upper surface of the culture plate (2); an advancing device (14) of the slide (4) configured such as to enable obtaining
(Continued)

a constant and substantially vibration-free advancing speed of the slide (4) in the image-acquiring zone; and an electronic control device (9) of a functioning of the camera (6), of the lighting device and of the advancing device (14).

20 Claims, 5 Drawing Sheets

(51) Int. Cl.
*C12M 1/26* (2006.01)
*C12M 1/00* (2006.01)
*C12M 1/34* (2006.01)
*C12N 1/20* (2006.01)

(58) Field of Classification Search
CPC ... C12M 41/46; C12N 1/20; G01N 35/00029; G01N 35/00732; G01N 21/8901; G01N 21/95684; G01N 21/9501; G01N 2201/0635; G01N 2021/845; B07C 5/3404; B07C 5/3422; G02B 13/22; Y10S 209/922
See application file for complete search history.

(56) References Cited

U.S. PATENT DOCUMENTS

| | | |
|---|---|---|
| 2002/0090320 A1 | 7/2002 | Burow et al. |
| 2003/0044321 A1 | 3/2003 | Haslam et al. |
| 2004/0101952 A1 | 5/2004 | Vent |
| 2004/0102903 A1* | 5/2004 | Graessle ............ G01N 15/1475 702/19 |
| 2005/0053265 A1 | 3/2005 | Graessle et al. |
| 2009/0042281 A1 | 2/2009 | Chang et al. |
| 2009/0078620 A1* | 3/2009 | Malek ................ B07C 5/3404 209/701 |
| 2011/0150314 A1 | 6/2011 | Bolea |
| 2012/0275681 A1* | 11/2012 | Honda ................ C12M 33/00 382/133 |
| 2014/0293036 A1* | 10/2014 | Ddecaux ............ G01N 21/255 348/80 |

FOREIGN PATENT DOCUMENTS

| | | |
|---|---|---|
| JP | 2003513251 A | 4/2003 |
| JP | 2003135095 A2 | 5/2003 |
| JP | 2006508362 A | 3/2006 |
| JP | 2011103786 A | 6/2011 |
| JP | 2012039930 | 3/2012 |
| JP | 2016509582 A | 3/2016 |
| WO | WO2012066101 A1 | 5/2012 |
| WO | WO2012150555 | 11/2012 |
| WO | WO2012152769 A1 | 11/2012 |

OTHER PUBLICATIONS

European Patent Office, Communication Pursuant to Article 94(3) EPC, European Application No. 14 728 321,2, dated Mar. 15, 2017, 8 pages.

* cited by examiner

DEVICE AND METHOD FOR AUTOMATIC PROCESSING OF CULTURE PLATES FOR MICROBIOLOGICAL SAMPLES

CROSS-REFERENCE TO RELATED APPLICATIONS

This application is a U.S. National Phase Application under 35 U.S.C. § 371 and claims the benefit of priority to International Patent Application Serial No. PCT/IB2014/060993, filed on Apr. 23, 2014, which claims the benefit of priority to Italian Patent Application Serial No. MI2013A000692, filed on Apr. 26, 2013, the contents of which are hereby incorporated by reference.

DESCRIPTION

The concepts herein relate to a device and a process for automatic processing of culture plates for microbiological samples, as well as an apparatus for automatic treatment of culture plates for microbiological samples comprising the processing device.

The concepts herein in particular are applicable for automatically transferring is culture plates, such as Petri dishes and the like, from a manual seeding zone or from an apparatus for automatic seeding of microbiological samples on the plates towards an incubator, as well as processing and enabling automation at least in part of an analysis of the plates after extraction from the incubating storage.

The most well-known and widely-used container for solid and semi-solid culture media, on which bacterial colonies can be grown using various methods, is the Petri dish, and consists in a plate, previously sterilized and filled for example with agar (liquefied culture medium) which when cooling solidifies and takes on the cylindrical shape of the recipient.

Therefore the use of Petri dishes is known for seeding microbiological samples, for example comprising bacteria, on culture media, for example for enabling a subsequent analysis of any eventual growth of bacterial colonies on the media with the aim of identifying the bacteria present in the biological sample and other characteristics of the biological sample.

Also known are apparatus that enable automation of various steps of the above-described process, for example the apparatus termed WASP™, realized by the present Applicant, has enabled a significant degree of the seeding process of microbiological samples on the culture plates.

After seeding, the culture plates are inserted in an incubator, for a predetermined period of time, for example 24 hours, after which they are analysed to verify the eventual presence of bacterial colonies or other biological functions, so as to acquire information relating to the biological sample deposited on the plate, for example with the aim of identifying the most suitable treatment for a patient.

These known solutions therefore include an analysis of each plate by a doctor or a highly-specialised laboratory operator, and this constitutes a critical step in the overall process which is highly critical. The critical aspects comprise for example a risks of human error, poor repeatability, the absence of traceability over time of the analysed sample, long laboratory times for enabling a sufficient incubation so as to enable correct identification of the sample, low efficiency and very high costs. To obviate these problems to some extent, partly-automated devices have been developed which enable obtaining digital images of the plates collected from the incubator, in such a way as to enable maintaining a trace of the bacterial growth verified on each dish and help in some way the work of the doctors and specialized laboratory staff These known solutions, however, also exhibit numerous drawbacks, as for example they do not enable obtaining a quality of the detected images that is sufficient to lead to a reliable analysis based on only the images, do not enable reducing the incubation times, only modestly increase the efficiency of the system and further incur high costs.

In certain instances, the concepts herein obviate one or more of the problems encountered in the prior art.

In certain instances, the concepts herein provide a device and a process for automatic processing of culture plates for microbiological samples which enable obtaining images of very high quality.

In certain instances, the concepts herein provide a device and a process which enable varying the type of images obtained for adapting them to the analyses to be performed and facilitate the analysis and/or obtain images specifically suited to highlighting the characteristics of interest in the microbiological samples.

In certain instances, the concepts herein provide a device and a process which enable reducing the incubation times required for enabling a correct identification of the sample, and therefore enable carrying out analysis of the sample in a shorter time.

In certain instances, the concepts herein provide a device and a process exhibiting high productivity and overall efficiency of the process.

In certain instances, the concepts herein provide a device and a process enabling a reliable analysis even when based only on images of the culture plate.

In certain instances, the concepts herein provide a device and a process enabling automating as much as possible the manipulating and transferring procedures and the analysis of the microbiological samples.

In certain instances, the concepts herein provide a device and a process for enabling facilitating the analysis and recognition work of the samples, and is which reduce the risk of human error.

In certain instances, the concepts herein provide a device and a process which enable reducing the risk of contamination of the collected samples.

In certain instances, the concepts herein provide a device and a process which offer high traceability of the collected samples.

In certain instances, the concepts herein provide a device and a process which are simple to use and easy to actuate.

In certain instances, the concepts herein disclose a device and a process that incur costs that are not high and that are suitable for enabling wide use thereof.

These aims and others besides, which will more fully emerge from the following description, are substantially attained by a device and a method according to what is expressed in one or more of the appended claims, taken alone or in any combination among themselves or in any combination with one or more of the further aspects described in the following.

Therefore further aspects will be described in the following, each of which can be taken independently or in combination with any one of the appended claims and/or the further aspects described in the following.

In a first further aspect, the concepts herein encompass a processing device of culture plates, in which the culture plates exhibit a diameter comprised between 10 and 250 mm, or between 50 and 150 mm, or between 70 and 100 mm and the seating of the slide is configured for housing a plate having these dimensions.

In a second aspect, the concepts herein encompass a processing device configured for carrying out, for each plate, at least 2000, or at least 3000, or at least 4000, or at least 5000 linear images for each colour, which are composed so as to obtain a corresponding number of multi-coloured linear images, in turn combined such as to obtain an overall image of the culture plate.

In a third aspect, the concepts herein encompass a processing device in which the resolution of the camera is at least 500 pixel, or at least 1000 pixel, or at least 1500 pixel per colour per $mm^2$ of plate surface and/or at least 1500 pixel, or at least 3000 pixel, or at least 4500 pixel overall per $mm^2$ of plate surface.

In a fourth aspect, the concepts herein encompass a processing device in which the dimension of each pixel of the resolution of the camera is comprised between 5 and 60 μm, or between 10 and 40 μm, or between 20 and 30 μm.

In a fifth aspect, the concepts herein encompass a processing device in which the overall resolution of the camera is preferably at least 5, or at least 10 or at least 15 or at least 20 Megapixel per colour and/or preferably at least 15, or at least 30, or at least 45 or at least 60 Megapixel overall.

In a sixth aspect, the concepts herein encompass a processing device in which the monochromatic linear sensors are configured for respectively detecting the colors blue, green and red.

In a seventh aspect, the concepts herein encompass a processing device in which the camera and/or the first lighting device and/or the second lighting device are regulatable so as to vary the horizontal position thereof and/or the vertical position thereof and/or the inclination thereof, or wherein the first or the second lighting device have a power of at least 10 W, or at least 20 W, or at least 30 W.

In an eighth aspect, the concepts herein encompass a process for automatic processing of culture plates for microbiological samples further comprising the step of inferiorly illuminating the culture plate, on an opposite side to the camera, at least in the image acquiring zone.

In a ninth aspect, the concepts herein encompass a process in which the step of illuminating the plate superiorly and/or inferiorly is carried out by LED lighting and/or by a substantially linear light beam.

In a tenth aspect, the concepts herein encompass a process in which the step of superiorly illuminating the plate is performed by projecting a beam of light inclined by at least 10°, or at least 20°, or at least 30° with respect to the vertical axis.

In an eleventh aspect, the concepts herein encompass a process in which the step of illuminating the plate is performed only superiorly without a lower illumination and/or with the aid of a panel of a uniform colour, preferably white and opaque, positioned below the culture plate, or only inferiorly without superior illumination or by a simultaneous superior and lower illumination.

In a twelfth aspect, the concepts herein encompass a process further comprising steps of detecting, with each activation of the tv camera, three monochromatic linear images and combining the monochromatic linear images to obtain corresponding multi-coloured linear images each made up of three monochromatic linear images and/or wherein the images are captured with a timing of less than $1/1000$ seconds, or less than $1/2000$ seconds and preferably less than $1/3000$ seconds.

In a thirteenth aspect, the concepts herein encompass a process comprising a step of assembling the linear images into overall images of the culture plate and preferably also of a portion of the slide or the step of assembling the multi-coloured linear images into overall multi-colored images of the culture plate, and preferably also a portion of the slide.

In a fourteenth aspect, the concepts herein encompass a process further comprising a step of obtaining a first initial overall image of the culture plate obtained in a first step before a period of incubation of a biological sample arranged on the culture plate and a successive first overall image obtained in a second step following a period of incubation of the biological sample on the culture plate and/or carrying out an analysis or a differential processing between the first overall successive image and the first overall initial image in order to produce a differential overall image containing information relating to differences detected between the first initial overall image and the first successive overall image and/or the step of memorizing the images for a future use.

In a fifteenth aspect, the concepts herein encompass a process further comprising a step of obtaining a first initial image of the plate in a first step prior to a period of incubation of a biological sample arranged on the plate and a plurality of successive overall images of the culture plate obtained in a corresponding plurality of steps posterior to corresponding periods of incubation for a corresponding plurality of time intervals and/or carrying out an analysis or differential processing between the plurality of successive overall images and the first initial overall image such as to produce a plurality of overall differential images containing information relating to the differences detected between the first overall initial image relative to the differences detected between the first initial overall image and the plurality of successive overall images.

In a sixteenth aspect, the concepts herein encompass a process further comprising the step of verifying the exact position of the slide with respect to the camera or determining any possible correction of the images acquired by the camera or determining the exact angular positioning of the culture plate on the slide by an automatic detection of the position of two reference elements, or reference holes of the plate.

In a seventeenth aspect, the concepts herein encompass a process further comprising a step of detecting a reflected image of a bar code or another informative element of the plate for determining an exact angular positioning of the culture plate on the slide using the bar code as a positioning reference and memorizing a datum relative to the exact angular positioning of the culture plate so as to enable a precise comparison with overall successive images of the plate, taking out of any angular displacements of the culture plate between an image and another.

In an eighteenth aspect, the concepts herein encompass a process comprising a step of further obtaining a first and a second initial overall image of the culture plate in the first step prior to an incubation period, the first and the second initial overall image being obtained in illuminated conditions of the plate respective different and/or selectively with or without the presence of the uniform colour panel positioned below the culture plate.

In a nineteenth aspect, the concepts herein encompass a process comprising a step of further obtaining a first and a second successive overall image of the culture plate in a same step following an incubation period, the first and the second successive overall image being obtained in illuminated conditions of the plate respectively different and/or selectively with or without the presence of the uniform colour panel positioned below the culture plate.

In a twentieth aspect, the concepts herein encompass an automatic processing device of culture plates for microbiological samples, in which the device comprises a slide or shuttle provided with a seating configured for removably is housing a culture plate for microbiological samples, movably mounted on the support frame so as to be selectively displaceable between a first loading position, an image-acquiring position, and a first unloading position.

In a twenty-first aspect, the concepts herein encompass a processing device further comprising a camera, provided with an optic, preferably of a linear type, and a sensor, preferably of a trilinear type, and arranged so as to acquire, at an image-acquiring zone, an image of an upper surface of the culture plate housed on the slide.

In a twenty-second aspect, the concepts herein encompass a processing device further comprising a further lighting device orientated in such a way as to illuminate the upper surface of the culture plate, at the image-acquiring zone.

In a twenty-third aspect, the concepts herein encompass a processing device further comprising an advancing device of the slide configured for advancing the slide towards or through the image-acquiring zone.

In a twenty-fourth aspect, the concepts herein encompass a processing device further comprising an electronic control device of the functioning of the camera and/or the first lighting device and/or the second lighting device and/or the advancing device.

In a twenty-fifth aspect, the control device comprises a data memory and is configured for memorizing some of the detected images.

A detailed description now follows, by way of non-limiting example, of one or more examples, in which:

FIG. 4 is a schematic frontal view of some elements of the device of FIG. 2a;

With reference to the accompanying figures, 1 denotes in its entirety an automatic processing device of culture plates 2 for microbiological samples, for example bacteriological. For example, the microbiological samples arranged on the culture plates can comprise various types of bacteria, present for example in biological samples such as samples of urine, pharyngeal or vaginal samples collected using a tampon bud, faecal samples, etc. In the present description, "culture plate" is taken to mean, for example, preferably Petri dishes, or alternatively slides for Gram staining or other like supports used in microbiological and/or bacteriological analysis.

The processing device 1 can comprise at least a support frame 3. The processing device 1 can also comprise at least a slide 4 or shuttle provided with a seating 5 configured for removably housing, in a horizontal position, at least a culture plate 2 for microbiological samples. The culture plate 2 can for example exhibit a diameter of between 10 and 250 mm, or between 50 and 150 mm, or between 70 and 100 mm, preferably 90 mm, and the seating 5 of the slide 4 is configured for housing a culture plate 2 having those dimensions. The slide 4 can be movably mounted on the support frame 3 so as to be selectively displaceable at least between a first loading position of the culture plate 2 on the slide 4 (illustrated in FIG. 2), a plurality of image-acquiring positions (two of which are illustrated in FIGS. 2a and 2b), and at least a first unloading position of the culture plate 2 from the slide 4 (illustrated in FIG. 2c).

The processing device 1 further comprises at least a camera, 6, preferably of a linear type, provided with at least an optic 7 preferably of a telecentric type and a preferably trilinear sensor (not illustrated in detail in the figures as of known type), i.e. made up of three linear sensors. The camera 6 is arranged in a vertical axis 8 so as to acquire, at an image-acquiring zone, a multiplicity of linear images of corresponding linear portions of an upper surface of the culture plate 2 housed on the slide 4, during the displacing of the slide 4. Each linear image is obtained at a relative position of the image-acquiring positions (for example FIGS. 2a and 2b illustrate two image-acquiring positions).

The trilinear sensor comprises three linear sensors, each of which able to detect a single colour, for example respectively red, green and blue, and acquire a relative monochromatic linear image of the image-acquiring zone. The camera 6 or the electronic control device 9 of the processing device 1 can be configured for combining the monochromatic linear images in order to obtain corresponding multicoloured linear images of the image acquiring zone, each composed of three monochromatic linear images. Each linear image can correspond to a substantially linear portion of the culture plate 2 having a thickness comprised between 50 and 500 µm, or between 100 and 300 µm, or between 150 and 200 µm. The trilinear sensor is preferably arranged such as to detect a linear image arranged perpendicularly to an advancing direction 10 of the slide 4 between the image-acquiring positions. The telecentric optic 7 is preferably configured for providing a depth of field of at least 5 mm, or at least 10 mm, or at least 15 mm, or at least 20 mm, and positioned substantially at the surface of the culture plate 2, such as also to maintain both the surface of the culture plate 2 and the culture medium, as well as any reliefs of a biological origin arranged on the surface, in focus. The overall images of the plate to which reference is made in the present description are preferably coloured or s multicoloured overall images. The processing device 1 can be configured for performing, for each culture plate 2, at least 2000, or at least 3000, or at least 4000, preferably at least 5000 linear images for each color, which are composed such as to obtain a corresponding number of multi-coloured linear images, in turn combined such as to obtain an overall image of the culture plate 2.

The resolution of the camera 6 can be at least 500 pixel, or at least 1000 pixel, or at least 1500 pixel per colour per $mm^2$ of surface of the culture plate 2 and/or at least 1500 pixel, or at least 3000 pixel, or at least 4500 pixel overall per $mm^2$ of surface of the culture plate 2.

The dimension of each pixel of the resolution of the camera 6 can be for is example comprised between 5 and 60 µm, or between 10 and 40 µm, or between 20 and 30 µm.

The resolution of the camera 6 is preferably about 3, or at least 6 or at least 9 Megapixel or at least 12 Megapixel per colour and/or preferably at least 9, or at least 18, or at least 27 Megapixel equivalent on the surface of a culture plate 2 with a 90 mm diameter. The overall resolution of the camera 6 is preferably at least 5, or at least 10 or at least 25 or at least 20 Megapixel per colour and/or preferably at least 15, or at least 30, or at least 45 or at least 60 Megapixel overall.

The processing device 1 can further comprise at least a first lighting device 11, preferably mounted on the support frame 3 in a laterally-displaced position with respect to the camera 6. The lighting device is preferably orientated inclined with respect to the vertical axis 8 in such a way as to illuminate at least the linear portions of an upper surface of the culture plate 2, at least at the image-acquiring zone. The first lighting device 11 can be orientated in such a way as to project a beam of light inclined by at least 10°, or at least 20°, or at least 30° with respect to the vertical axis 8 along which the camera 6 is arranged. The first lighting device 11 can be mounted with an adjustable inclination. The first lighting device 11 can be able to project a substantially linear light beam onto the culture plate 2.

The processing device 1 can further comprise at least a second lighting device 12, preferably mounted on the support frame 3 and/or orientated such as to illuminate a lower surface of the culture plate 2, opposite the camera 6, at least at the image acquiring zone. The second lighting device 12 can be mounted in an aligned position with the camera 6. The first and/or the second lighting device 12 can comprise at least a first plurality of LEDs arranged linearly and/or along a direction substantially perpendicular to an advancing direction 10 of the slide 4 in the image-acquiring zone.

Owing also to the additional lighting provided by the second lighting device 12, useful in particular in the case of transparent plates, it is possible to improve the recognisability of the biological structures 26, for example bacterial colonies, is which develop on the culture medium, and reduce the incubation time required for carrying out a diagnosis. In particular the first and/or the second lighting device 12 can comprise a row of LEDs. The first and/or the second lighting device 12 can have a power of at least 10 W, or at least 20 W, or at least 30 W.

Figure 1:
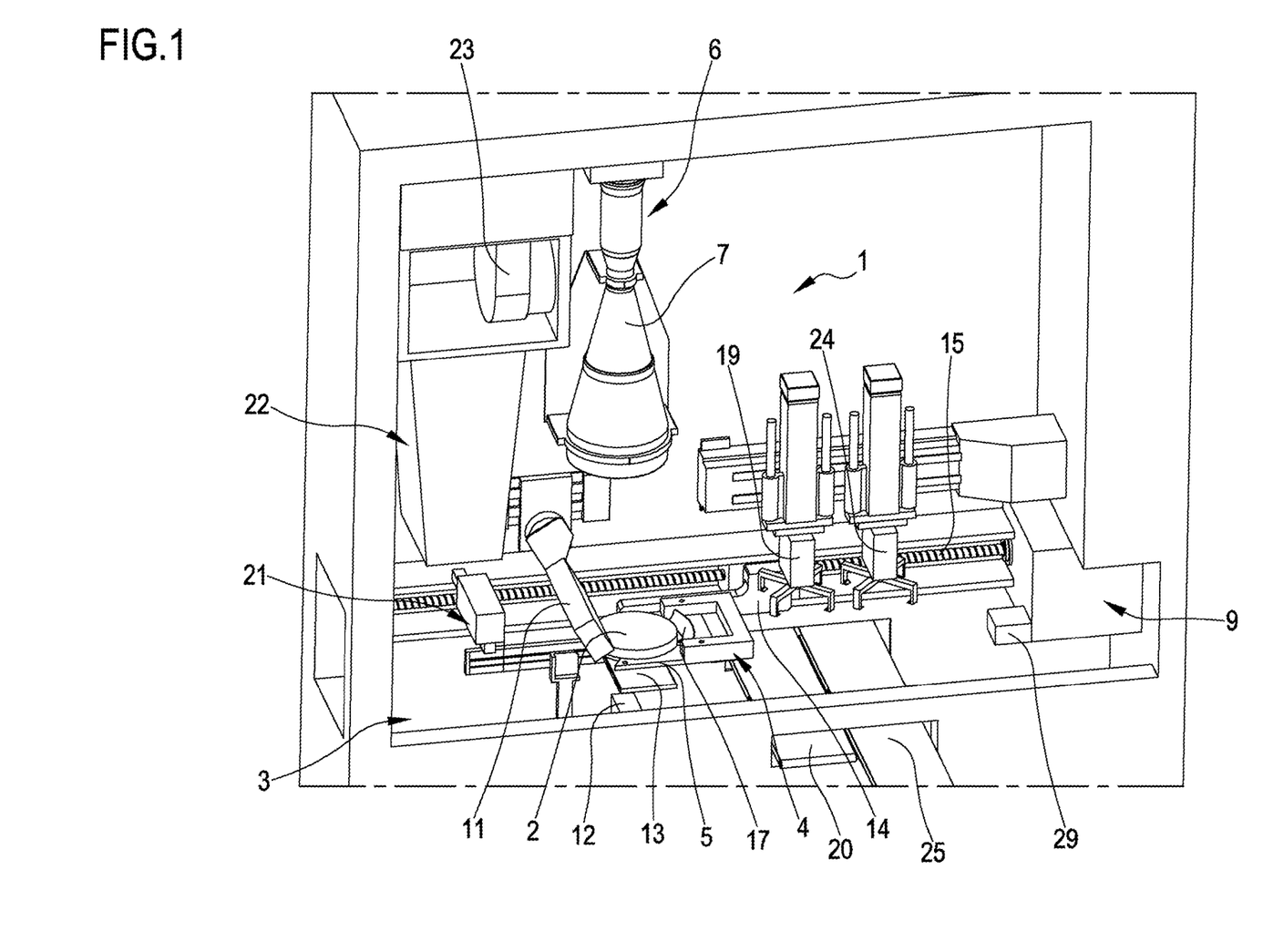
FIG. 1 is a perspective view of an example device according to the concepts herein.
Figure 2:
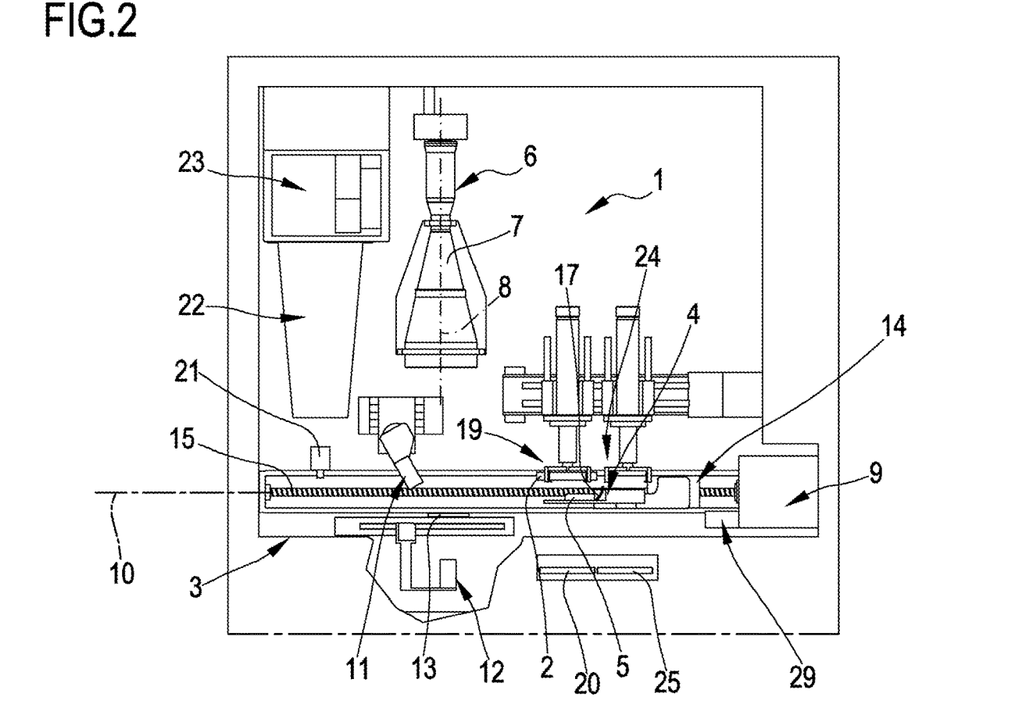
FIGS. 2, 2a, 2b and 2c show a frontal view of the example, corresponding to various operating positions of a housing slide of a culture plate.
Figure 2A:
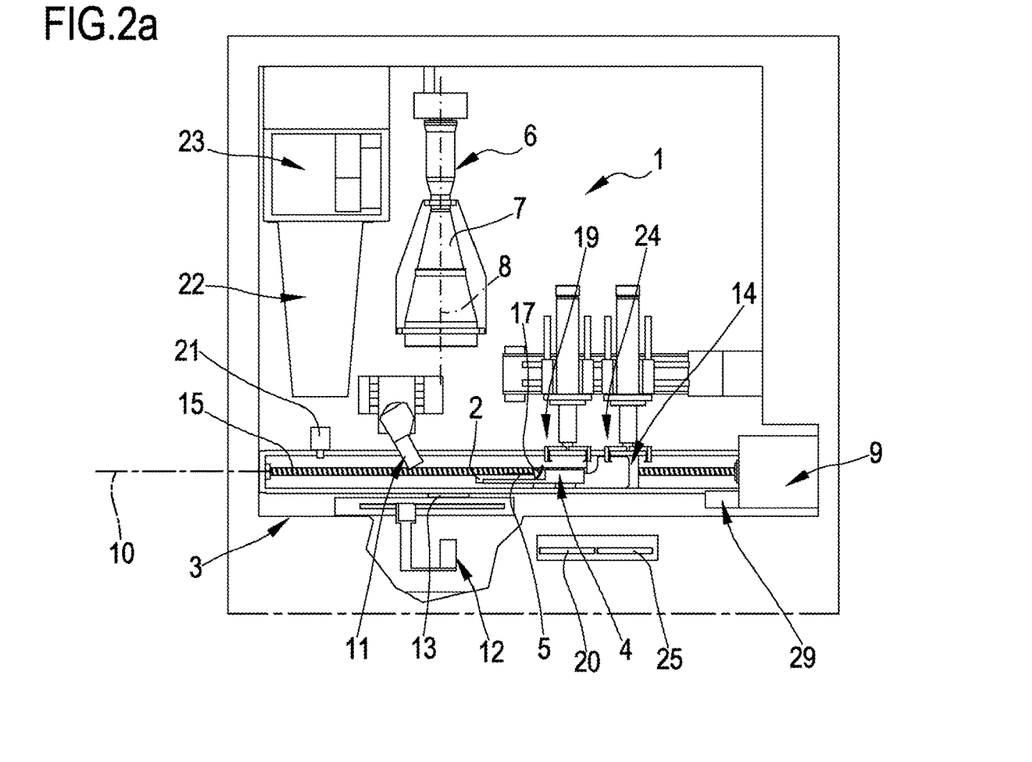
Figure 2B:
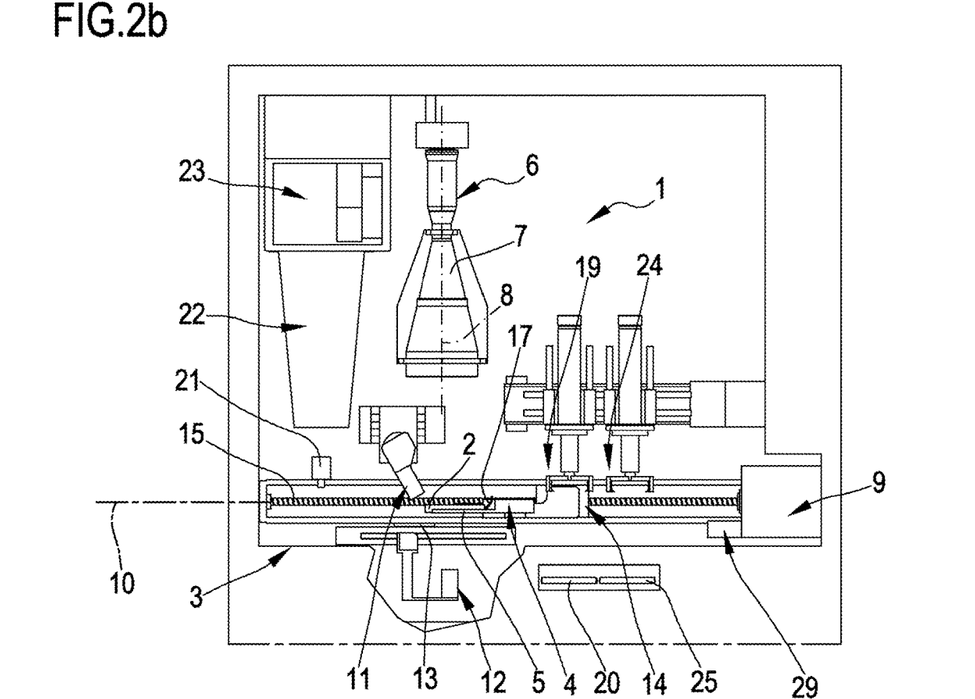
Figure 2C:
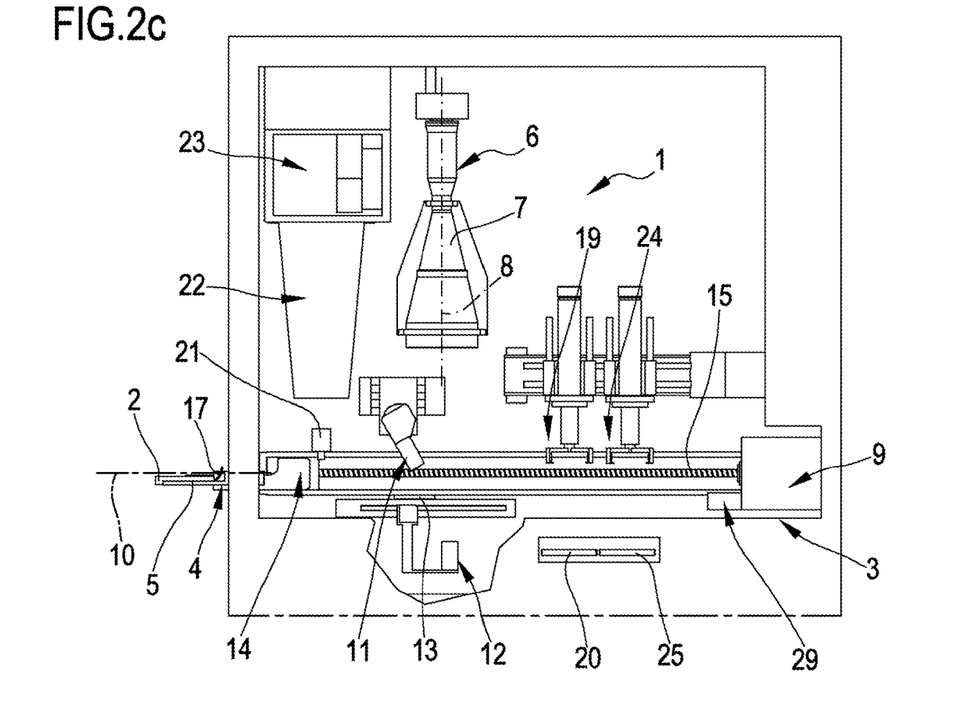
Figure 3:
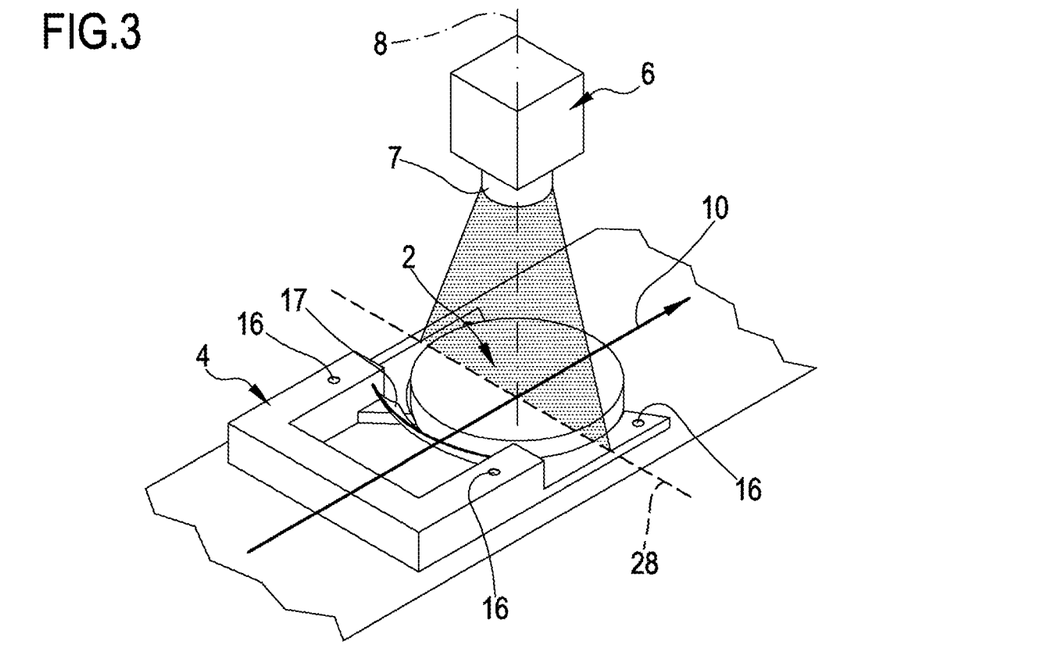
FIG. 3 is a schematic perspective view representing the functioning of some elements of the device of FIG. 1.
Figure 4:
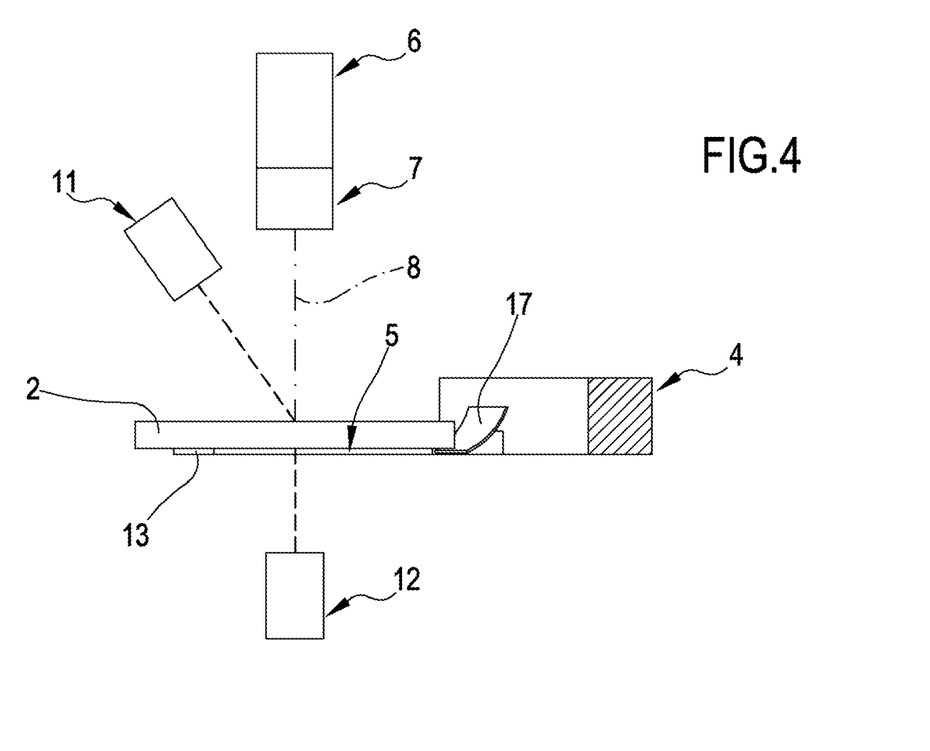

The processing device 1 can further comprise at least a panel 13 having a uniform colour, preferably white and opaque, movably mounted so as to be selectively positionable below the culture plate 2 at the image-acquiring positions in order to improve the image detected by the camera 6 in the first operating condition (as illustrated in FIGS. 1, 2 and 2a). The panel is further selectively positionable in an inactive position (illustrated in FIGS. 2b and 2c) in which it is displaced laterally with respect to the axis of the camera in such a way as not to intervene in the detecting process of the image of the plate and further in such a way as to enable illuminating the plate 2 from below by the second lighting device 12.

The processing device 1 can further comprise at least an advancing device 14 of the slide 4, preferably configured such as to enable obtaining a constant and substantially vibration-less advancing speed of the slide 4 at least in the image-acquiring zone. The advancing device 14 preferably comprises at least an endless screw 15 to which it is movably connected and from which the slide 4 is drawn. The advancing device 14 further comprises at least an encoder for controlling the advancing of the slide 4. The encoder can be connected to the control device 9 such as to enable determining the correct detection frequency of the linear images by the camera 6.

The processing device 1 can further comprise at least an electronic control device 9 of the functioning at least of the camera 6 and/or of the first lighting device 11 and/or of the second lighting device 12 and/or of the advancing device 14 and/or of the panel 13. The control device 9 can be configured for defining a plurality of operating conditions of the lighting devices, in particular at least a first operating condition in which only the first lighting device 11 is active, a second operating condition in which only the second lighting device 12 is active and/or at least a third operating condition in which both the first and the second lighting device 12 are active so as to illuminate the culture plate 2.

The camera 6 or the electronic control device 9 can be configured for assembling the multicolored linear images in overall images at least of the culture plate 2 and at least a portion of the slide 4.

Figure 5:
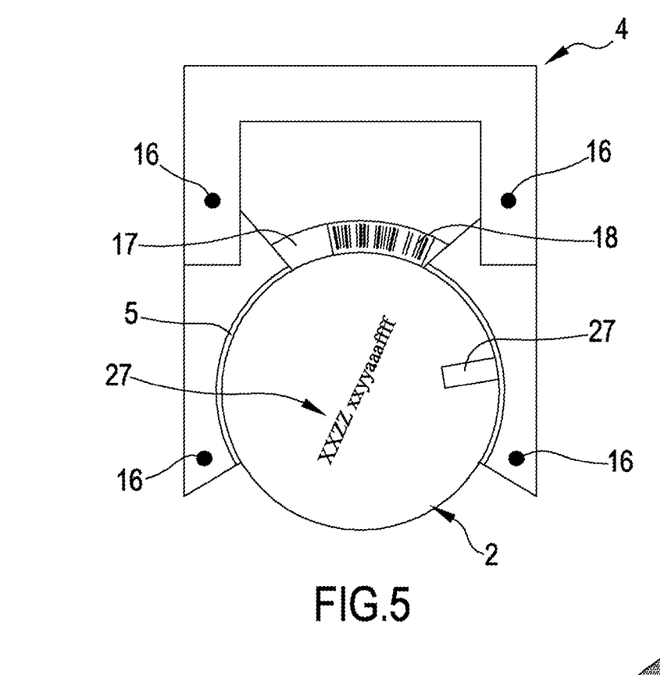
FIG. 5 is an initial overall image from above of a culture plate housed in a slide of the device of FIG. 1.
Figure 6:
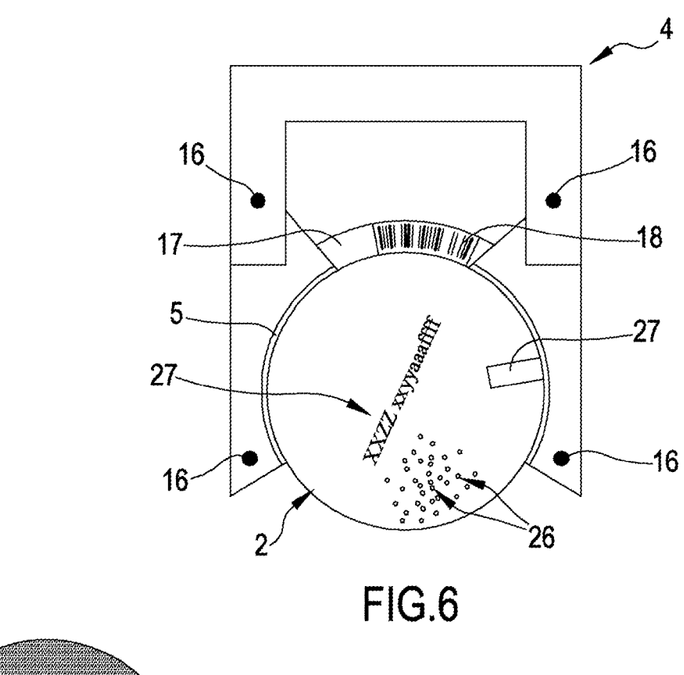
FIG. 6 is a successive overall image corresponding to the image of FIG. 5 and relative to the same plate after a determined incubation period.

The electronic control device 9 can be configured for obtaining at least a first overall initial image (for example illustrated in FIG. 5) of the culture plate 2 obtained in a first step before a period of incubation of a biological sample arranged on the culture plate 2 and at least a successive first overall image (for example illustrated in FIG. 6) obtained in at least a second step following a period of incubation of the biological sample on the culture plate 2 for a first time period.

The control device 9 can be further configured for performing an analysis or differential processing at least between the first overall successive image and the first overall initial image in order to produce at least a differential overall image (for example illustrated in FIG. 7) containing information relating to differences detected between the first initial overall image and the first successive overall image.

Figure 7:
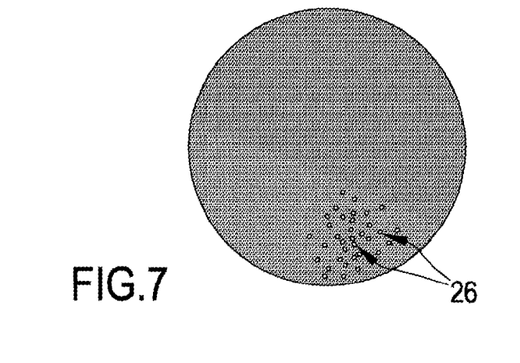
FIG. 7 is a differential image processed by subtracting the information of FIG. 5 from the information of FIG. 6.

The overall differential image therefore evidently shows only the variations that have occurred in the time period between the first and the first successive image, and therefore the bacterial cultures and the like which have been produced on the culture plate 2. The overall differential image does not, on the other hand, exhibit other undesired disturbing elements 27 such as for example writing, scratches, marks, which are instead present in the first and the first successive overall image and which make it very difficult to recognize desired information relative to the bacterial growths or the like.

The electronic control device 9 can be configured for further obtaining a plurality of successive overall images of the culture plate 2 obtained in a corresponding plurality of steps following corresponding incubation periods for a plurality of time intervals and/or for carrying out an analysis or differential processing between the plurality of overall successive images and the first initial overall image such as to produce at least a plurality of overall differential images containing information relating to the differences detected between the first initial overall image and the plurality of successive overall images.

The slide 4 is preferably provided with at least two reference elements, or reference holes 16, enabling the control device 9 to verify the exact position of the slide 4 with respect to the camera 6 and to determine any possible correction of the images acquired by the camera 6 and to determine an eventual correction of the images acquired or to determine the exact angular positioning of the culture plate 2 on the slide 4.

The slide 4 is further provided with at least a reflective element 17 arranged in proximity of the seating 5 for the culture plate 2 on the slide 4 and configured for projecting an image of a lateral portion of the culture plate 2, provided with a bar code 18, towards the camera 6. The control device 9 is preferably configured for determining the exact angular positioning of the culture plate 2 on the slide 4 using the bar code 18 as an angular positioning reference. The control device 9 can further be configured for memorizing a datum relating to the exact positioning and for utilizing the datum relative to the exact positioning to enable an exact comparison between overall images carried out before incubation and overall images carried out at different steps of the incubation.

The concepts herein further relate to an apparatus for automatically treating culture plates 2 for microbiological samples.

The concepts herein encompass an automatic processing device of culture plates 2 for microbiological samples of the above-described type.

The apparatus can further comprise a device for automatic seeding (not illustrated as of known type) of microbiological samples on the culture plates 2, positioned upstream of the processing device 1.

The apparatus can further comprise a device for automatic labelling (not illustrated as of known type) of each of the culture plates 2, in particular by applying bar codes.

The apparatus can further comprise a first handler 19 able to position the culture plates 2, coming from a first conveyor belt 20 in arrival from the automatic seeding device, in the seating 5 of the slide 4.

The apparatus can further comprise an incubation storage (not illustrated as of known type) for the culture plates 2, located downstream of the processing device 1.

The apparatus can further comprise a second handler able to position the plates, coming from the processing device 1 and arranged on the slide 4, in the incubating storage and/or to collect the plates from the incubation storage after a predetermined time interval such as to reposition them in the seating 5 of the slide 4.

The apparatus can further comprise an automatic and selective opening and/or closing device 21 for opening and/closing the plates with a relative cover.

The apparatus can further comprise an air aspirator 22 and a filter 23, in particular of a HEPA type, able to purify the air at least at the opening device 21 of the plates.

The apparatus can further comprise a third handler 24 able to collect the plates in outlet from the processing device 1 for unloading the plates or for sending them towards a manual work station thereof by a second conveyor belt 25.

The apparatus can further comprise a bar code reader 29 able to read the bar codes of the culture plates in inlet and/or in outlet from the processing device and connected to the control device so as to enable the tracing of the processed culture plates and the exact associated between images and samples. The culture plate can be brought to the bar code reader 29 by raising and rotating devices associated to the frame (not illustrated as of known type), or directly by a handler.

The concepts herein encompass a process for automatically processing culture plates 2 for microbiological samples, comprising at least a step of automatically moving a culture plate 2 for microbiological samples positioned, preferably, in a horizontal position on a slide 4 or shuttle at least between a loading position of the culture plate 2 on the slide 4 at least between a loading position of the culture plate 2 on the slide 4, at least an image-acquiring position and preferably a plurality of image-acquiring positions, and at least an unloading position of the culture plate 2 from the slide 4, preferably maintaining an advancing velocity that is constant and substantially vibration-free, at least in the image-acquiring zone.

The process further preferably comprises at least a step of at least superiorly illuminating the culture plate 2 at least at an image-acquiring zone.

The process further preferably comprises at least the step of acquiring at least an overall image of the culture plate 2, and preferably a multiplicity of linear images, of corresponding linear portions of the culture plate 2 in the image-acquiring zone, each linear image being obtained at one of the image-acquiring positions, during the advancing of the slide 4, preferably by a linear-type camera 6 arranged vertically above the slide 4 and provided at least with an optic, preferably of the telecentric type and a sensor preferably of the trilinear type. Obviously in a case where the processing device 1 is used for analysis of slides for Gram staining or other like supports used for microbiological and/or bacteriological analyses, there may or may not be use of an association with an incubation storage. Further an adapter can be included to be inserted in the slide for enabling a housing of the seating 5 of culture plates 2 having different dimensions to the standard dimensions (for example Gram-staining slides).

In the following, for the sake of clarity the functioning of the device illustrated in the accompanying drawings will be described, by way of non-limiting example.

Firstly, each culture plate 2 is seeded with biological material in a device for s automatic seeding, after which it is sent to the processing device 1 by the first conveyor belt 20. The bar code reader 29 reads the code applied to the culture plate and communicates it to the control device 9. The first handler 19 then positions the culture plate 2 in the seating 5 of the slide 4, and the slide 4 then advances towards the image-acquiring zone at the camera 6 position. The control device 9 manages the functioning at least of the camera 6, the first and second lighting device 12 and uniform colour panel 13 appropriately and according to the type of culture plate 2 and image desired (if illuminated only from above, with the uniform colour panel 13 below the culture plate 2, or if also illuminated from below without the uniform colour panel 13 below the is culture plate 2).

During the controlled advancing of the slide 4, the camera thus detects the linear images of the culture plate 2 before incubation, and a high-resolution first initial overall image is acquired of the culture plate 2 in the described way. The culture plate 2 is then closed with a cover by the selective opening device and/or the closing device 21 and is thereafter positioned in the incubation storage, by the second handler.

After a predetermined time, the culture plate 2 is removed from the incubation storage and positioned on the slide 4, after which the cover is removed and the control device 9 obtains a first successive overall image of the culture plate 2 in the way described in the foregoing. The control device 9 can therefore obtain also a differential overall image able to facilitate the analysis of the growth of biological material following incubation, identifying the biological structures 26 by eliminating the disturbing elements 27. At this point the culture plate 2 can be newly inserted in the storage for a further incubation period, or can be sent on towards the second handler which loads it on the second conveyor belt 25, towards the unloading position or towards a manual treatment station thereof.

In certain instances, the concepts herein enable obtaining one or more of the following advantages. Firstly, in certain instances, the concepts herein enable resolving one or more of the problems encountered in the prior art.

In certain instances, the concepts herein can enable obtaining images of the culture plates and the growth of biological material thereon of a very high quality.

In certain instances, the concepts herein enable adapting the type of images realized according to the specific analysis to be carried out and the specific type of sample, so as to facilitate the analysis.

In certain instances, the concepts herein enable obtaining images specifically adapted to highlight the characteristics of interest relating to the single microbiological samples. In certain instances, the concepts herein enable reducing the incubation time required for obtaining the desired information from the microbiological samples. In certain instances, the concepts herein enable a reliable analysis also based on only the images of the culture plates.

In certain instances, the concepts herein enable at least partly automating the analytic process of the images of the microbiological samples, as well as significantly automating the handling and processing procedures of the microbiological samples. In certain instances, the concepts herein can further reduce the risk of contamination of the pathogen agents and the risk of human error in the sample analysis and further offers a high level of traceability of the samples collected and the results of the relative analyses. In certain instances, the concepts herein are simple to use and relatively simple to actuate. Lastly, in certain instances, the concepts herein enable a cost that is not high in comparison to present costs of the analyses in question.

The invention claimed is:

1. An automatic processing device of culture plates for microbiological samples, wherein the processing device comprises:
   a support frame;
   a slide or shuttle provided with a seating configured for removably housing, in a horizontal position, a culture plate for microbiological samples, the slide being movably mounted on the support frame and configured to be selectively displaceable between a first loading position of the culture plate on the slide, a plurality of image-acquiring positions, and a first unloading position of the culture plate from the slide;
   a camera of a linear type, provided with an optic of a telecentric type and a trilinear sensor, and arranged according to a vertical axis, the camera being configured to acquire, at an image-acquiring zone, a multiplicity of linear images of corresponding linear portions of an upper surface of the culture plate housed on the slide, during the displacing of the slide, each linear image being acquired at a relative image acquiring position of the image-acquiring zone, the automatic processing device being configured to assemble the linear images obtaining overall images of the culture plate;
   a first lighting device mounted on the support frame configured to illuminate the linear portions of an upper surface of the culture plate, at the image-acquiring zone;
   an advancing device of the slide configured to provide a constant advancing speed and substantially vibrationless advancing movement of the slide in the image-acquiring zone; and
   an electronic control device, programmed to control the functioning of the camera, of the first lighting device and of the advancing device to acquire and assemble the multiplicity of linear images.

2. The processing device of claim 1, further comprising a second lighting device mounted on the support frame, orientated and configured to illuminate a lower surface of the culture plate, opposite the camera, at the image acquiring zone and wherein the second lighting device is mounted in an aligned position with the camera.

3. The processing device of claim 2, wherein the first or second lighting device comprise a first plurality of LEDs arranged linearly and along a direction substantially perpendicular to an advancing direction of the slide in the image-acquiring zone.

4. The processing device of claim 1, wherein the first lighting device is mounted in a laterally-displaced position with respect to the camera and orientated inclined with respect to the vertical axis and configured to illuminate the linear portions.

5. The processing device of claim 1, wherein the first lighting device is orientated and configured to project a beam of light inclined by at least 10°, or at least 20°, or at least 30° with respect to the vertical axis along which the camera is arranged and wherein the first lighting device is mounted with an adjustable inclination and wherein it is able to project a substantially linear light beam on the culture plate.

6. The processing device of claim 1, wherein the electronic control device is configured for defining a plurality of operating conditions of the lighting devices, in particular a first operating condition in which only the first lighting device is active, a second operating condition in which only the second lighting device is active and a third operating condition in which both the first and the second lighting devices are active to illuminate the culture plate.

7. The processing device of claim 1, wherein the processing device further comprises a panel having a uniform colour movably mounted so as to be selectively positionable below the culture plate at the image-acquiring positions in order to improve the image detected by the camera in the first operating condition.

8. The processing device of claim 1, wherein the trilinear sensor comprises three linear sensors, each of which is able to detect a single colour and acquire a relative monochromatic linear image of the image-acquiring zone and wherein the camera or the electronic control device are configured for combining the monochromatic linear images in order to obtain corresponding multicoloured linear images of the image acquiring zone, each composed of three monochromatic linear images and wherein each linear image corresponds to a substantially linear portion of the culture plate having a thickness comprised between 50 and 500 µm, or between 100 and 300 µm, or between 150 and 200 µm.

9. The processing device of claim 1, wherein the trilinear sensor is arranged such as to detect a linear image arranged perpendicularly to an advancing direction of the slide between the image-acquiring positions and wherein the telecentric optic is configured for providing a depth of field of at least 5 mm, or at least 10 mm, or at least 15 mm, or at least 20 mm, and positioned substantially at the surface of the culture plate, such as also to maintain any reliefs of a biological origin arranged on the surface in focus.

10. The processing device of claim 1, wherein the camera or the electronic control device are configured for assembling the multicolored linear images in overall images of the culture plate and of a portion of the slide.

11. The processing device of claim 1, wherein the electronic control device is configured for obtaining a first overall initial image of the culture plate obtained in a first step before a period of incubation of a biological sample arranged on the culture plate and a successive first overall image obtained in a second step following a period of incubation of the biological sample on the culture plate for a first time period.

12. The processing device of claim 1, wherein the electronic control device is further configured for carrying out an analysis or a differential processing between the first overall successive image and the first overall initial image in order to produce a differential overall image containing information relating to differences detected between the first initial overall image and the first successive overall image.

13. The processing device of claim 1, wherein the electronic control device is configured for further obtaining a plurality of successive overall images of the culture plate obtained in a corresponding plurality of steps following corresponding incubation periods for a plurality of time intervals and for carrying out an analysis or differential processing between the plurality of overall successive images and the first initial overall image such as to produce a plurality of overall differential images containing information relating to the differences detected between the first initial overall image and the plurality of successive overall images.

14. The processing device of claim 1, wherein the advancing device comprises an endless screw to which it is movably connected and from which the slide is drawn.

15. The processing device of claim 1, wherein the advancing device comprises an encoder for controlling the advancing of the slide, the encoder being connected to the electronic control device such as to enable determining the correct detection frequency of the linear images by the camera.

16. The processing device of claim 1, wherein the slide is provided with two reference elements, or reference holes, enabling the electronic control device to verify the exact position of the slide with respect to the camera and to determine any possible correction of the images acquired by the camera or to determine the exact angular positioning of the culture plate on the slide.

17. The processing device of claim 1, wherein the slide is provided with a reflective element arranged in proximity of the seating for the culture plate on the slide and configured for projecting an image of a lateral portion of the culture plate, provided with a bar code, towards the camera, the electronic control device being configured for determining the exact angular positioning of the culture plate on the slide using the bar code as an angular positioning reference.

18. The processing device of claim 1, wherein the electronic control device is configured for memorizing a datum relating to the exact positioning and for utilizing the datum relative to the exact positioning to enable an exact comparison between overall initial images carried out before incubation or subsequent overall images carried out at different steps of the incubation.

19. An apparatus for automatic treating of culture plates for microbiological samples, the apparatus comprising an automatic processing device of culture plates for microbiological samples according to claim 1 and further comprising one or more of the following elements:
- a device for automatically seeding microbiological samples on the culture plates, located upstream of the processing device;
- a labelling device for automatic labelling of each of the culture plates;
- a first handler able to position the culture plates, coming from the automatic seeding device, in the seating of the slide;
- an incubation storage for the culture plates, located downstream of the processing device;
- a second handler able to position the plates, coming from the processing device and arranged on the slide, in the incubating storage and to collect the plates from the incubation storage after a predetermined time interval such as to reposition them in the seating of the slide;
- an automatic and selective opening and closing device for opening and closing the plates with a relative cover;
- an air aspirator and a filter able to purify the air at the selective opening and closing device of the plates; and
- a third handler able to collect the plates in outlet from the processing device for unloading the plates or for sending them towards a manual work station thereof.

20. A process for automatic processing of culture plates for microbiological samples, comprising:
- automatically moving a culture plate for microbiological samples positioned in a horizontal position on a slide or shuttle between a loading position of the culture plate on the slide, a plurality of image acquiring positions, and an unloading position of the culture plate from the slide, maintaining a constant advancement velocity, and substantially without vibrations, in an image acquiring zone;
- superiorly illuminating the culture plate at the image acquiring zone; and
- acquiring a multiplicity of linear images of corresponding portions of the culture plate in the image acquiring zone, each linear image being obtained at one of the image acquiring positions, during the advancing of the slide, by a camera of a linear type, arranged vertically above the slide and provided with an optic of a telecentric type and a trilinear sensor.

* * * * *

UNITED STATES PATENT AND TRADEMARK OFFICE
CERTIFICATE OF CORRECTION

PATENT NO. : 10,550,362 B2
APPLICATION NO. : 14/787202
DATED : February 4, 2020
INVENTOR(S) : Daniele Triva Page 1 of 1

It is certified that error appears in the above-identified patent and that said Letters Patent is hereby corrected as shown below:

On the Title Page

Item (30) (Foreign Application Priority Data), Line 1, delete "MI2013A0692" and insert -- MI2013A000692 --;

Item (57) (Abstract), Line 7, after "arranged" insert -- to --.

Signed and Sealed this
Twelfth Day of May, 2020

Andrei Iancu
*Director of the United States Patent and Trademark Office*